United States Patent
Fornoff et al.

[11] Patent Number: 5,931,669
[45] Date of Patent: Aug. 3, 1999

[54] DENTAL APPARATUS HAVING ONE OR MORE DIFFERENTLY CONFIGURED INSTRUMENTS

[75] Inventors: Peter Fornoff, Reichelsheim; Josef Pabst, Heddesheim; Uwe Sauer, Worms; Ulrich Schulze-Ganzlin, Lorsch, all of Germany

[73] Assignee: Sirona Dental Systems GmbH & Co. KG, Bensheim, Germany

[21] Appl. No.: 08/407,948

[22] Filed: Mar. 22, 1995

[30] Foreign Application Priority Data

Mar. 22, 1994 [DE] Germany .......................... P 44 09 862

[51] Int. Cl.⁶ ...................................................... A61C 1/02
[52] U.S. Cl. .................................................. 433/28; 433/98
[58] Field of Search .................................. 433/28, 27, 98; 364/413.28

[56] References Cited

U.S. PATENT DOCUMENTS

| | | | |
|---|---|---|---|
| 4,305,126 | 12/1981 | Brier et al. | 433/28 |
| 4,308,011 | 12/1981 | Liefke | 433/28 |
| 4,915,626 | 4/1990 | Lemmey | 433/29 |
| 5,016,098 | 5/1991 | Cooper et al. | 433/29 |
| 5,052,924 | 10/1991 | Berg | 433/29 |
| 5,257,184 | 10/1993 | Mushabac | 364/413.28 |
| 5,401,170 | 3/1995 | Nonomura | 433/173 |

FOREIGN PATENT DOCUMENTS

0 391 967   8/1992   European Pat. Off. .

*Primary Examiner*—John J. Wilson
*Attorney, Agent, or Firm*—Hill & Simpson

[57] ABSTRACT

A dental apparatus is provided with a group of standard preparation instruments that are held in deposit devices having sensors allocated to each device to determine the configuration and deposit condition of the preparation instrument in the deposit device, the apparatus has a second group of non-preparation instruments which include image-acquiring instruments for diagnostic purposes. Both instrument groups or types share a personal computer with a keyboard and a monitor in common through one interface data where the instrument-related functions can be read in and read out so that the installed program of the personal computer is activated dependent on the particular instrument being used.

13 Claims, 2 Drawing Sheets

DENTAL APPARATUS HAVING ONE OR MORE DIFFERENTLY CONFIGURED INSTRUMENTS

BACKGROUND OF THE INVENTION

The present invention is directed to a dental apparatus which has one or more hand held preparation instruments or dental handpieces of different configurations that are held in deposit devices having allocated sensors that acquire the configuration and/or the deposit condition of each of the preparation instruments, instrument-related switches and display elements and a control means shared in common by the preparation instruments with whose assistance instrument-related functions can be displayed at a display and can be potentially activated with the assistance of a foot switch dependent on a removal or, respectively, deposit of an instrument.

An apparatus, which has a plurality of preparation instruments of different configurations that are held in deposit devices which include sensors for determining the position of and configuration of the particular preparation instrument, instrument-related switches and display elements and a control means shared in common by preparation instruments with whose assistance instrument-related functions can be displayed at the display and can be potentially activated with the assistance of a foot switch dependent on the removal and/or deposit of the instrument, is known and, for example, is disclosed in EP-B1-0 391 367. The known apparatus contains a plurality of holders for dynamic instruments, for example instruments provided with drive devices whose control and operating function can be displayed on a monitoring and control panel. A microprocessor is provided for this purpose. This microprocessor is designed so that a plurality of function display fields can be generated on the panel for the visual display of, on the one hand, instrument-related control functions and, on the other hand, auxiliary functions. An alpha-numerical keyboard can also be connected to the microprocessor, which makes it possible to display input information on the display fields. The monitoring and control panel can be a picture screen that can be utilized for displaying text and video information.

SUMMARY OF THE INVENTION

The present invention proceeds with an idea that hand-held instruments or handpieces, which can include either suction instruments or image-acquiring instruments, for example instruments having an integrated video camera for intraoral or extraoral observations in the patient mouth, can be utilized in a dental apparatus in addition to the above-mentioned dynamic hand-held instruments for drilling or grinding that primarily serve the purpose of preparation of the dental area.

The instruments or handpieces can also be differently configured. This means, for example, that they can be provided with various grip pieces (gearing heads, objective pieces and the like) or that different agents can be offered or, respectively, made available in these, for example with our without light, with or without spray.

The invention is based on the object of providing an apparatus having one or more preparation hand-held instruments of different configurations that are held in a deposit device which has allocated sensors that acquire the configuration and/or deposit condition, instrument-related switches, display elements and control means shared in common by the preparation instruments with whose assistance instrument-related functions can be displayed on the display element and be potentially activated with the assistance of a foot switch dependent on a removal or, respectively, deposit of the instrument, which further includes an additional group of hand-held non-preparation instruments, which preferably include image-acquiring instruments for diagnostic purposes and which instruments are heretofore exclusively integrated in autonomous, peripheral devices, so that the non-preparation instruments can be operated with economically justifiable outlay in addition to the standard preparation instruments and in the same way as the above-mentioned preparation instruments.

Inventively, the preparation instruments and the non-preparation instruments, which may provide diagnostic information, share a personal computer with a keyboard and picture screen in common, data from instrument-related functions being capable of being read in and out via one interface with the computer, whereby the program installed in the personal computer is activated dependent on the particular instrument configuration.

The present invention discloses a possibility of how peripheral devices that are customized to specific conditions and demands, such as hygiene, ergonomy, patient safety, etc., and that were hitherto arranged at a dental work station as autonomous devices can profit from new or different functions on the basis of a system integration at a personal computer, or PC.

According to an advantageous development of the invention, a logic circuit is present that, on the one hand, is connected to the interface of the personal computer and, on the other hand, is connected to the switch and display elements, whereby bidirectional operating data that corresponds to the instruments or, respectively, to the sensor values allocated to the instruments are transmitted via the logic circuit and the interface of the personal computer.

According to another advantageous development of the invention, the apparatus contains deposit holders allocated to the instruments, as well as position-indicating sensors allocated thereto, as known, for example, from U.S. Pat. No. 4,308,011. The logic circuit activates the personal computer in response to the removed instrument to effect the offering of a program allocated to that instrument.

Also advantageously, means can be provided that report the operating condition of the instrument-related drive, deviations from rated operating conditions or other error messages to the personal computer and potentially display them at the monitor. Thus, for example, the removal of the intraoral video camera can be indicated to the personal computer which, in turn, automatically activates the corresponding program. The user can be prompted by the program and initiate corresponding functions via controls or, respectively, switch elements at the camera or at a foot switch, as well. As soon as the instrument is placed back in its deposit, the original condition is restored. As already mentioned, peripheral information, particularly error messages as well, can be communicated via the logic circuit and displayed at the monitor of the personal computer.

Even though any standard interface, such as an ISA bus for plug-in cards, parallel or serial interfaces, multi-function interfaces can be used, it is advantageous to utilize a serial interface for the data transmission.

Other advantages and features of the invention will be readily apparent from the following description of the preferred embodiments, the drawings and claims.

DESCRIPTION OF THE PREFERRED EMBODIMENTS

Figure 1:
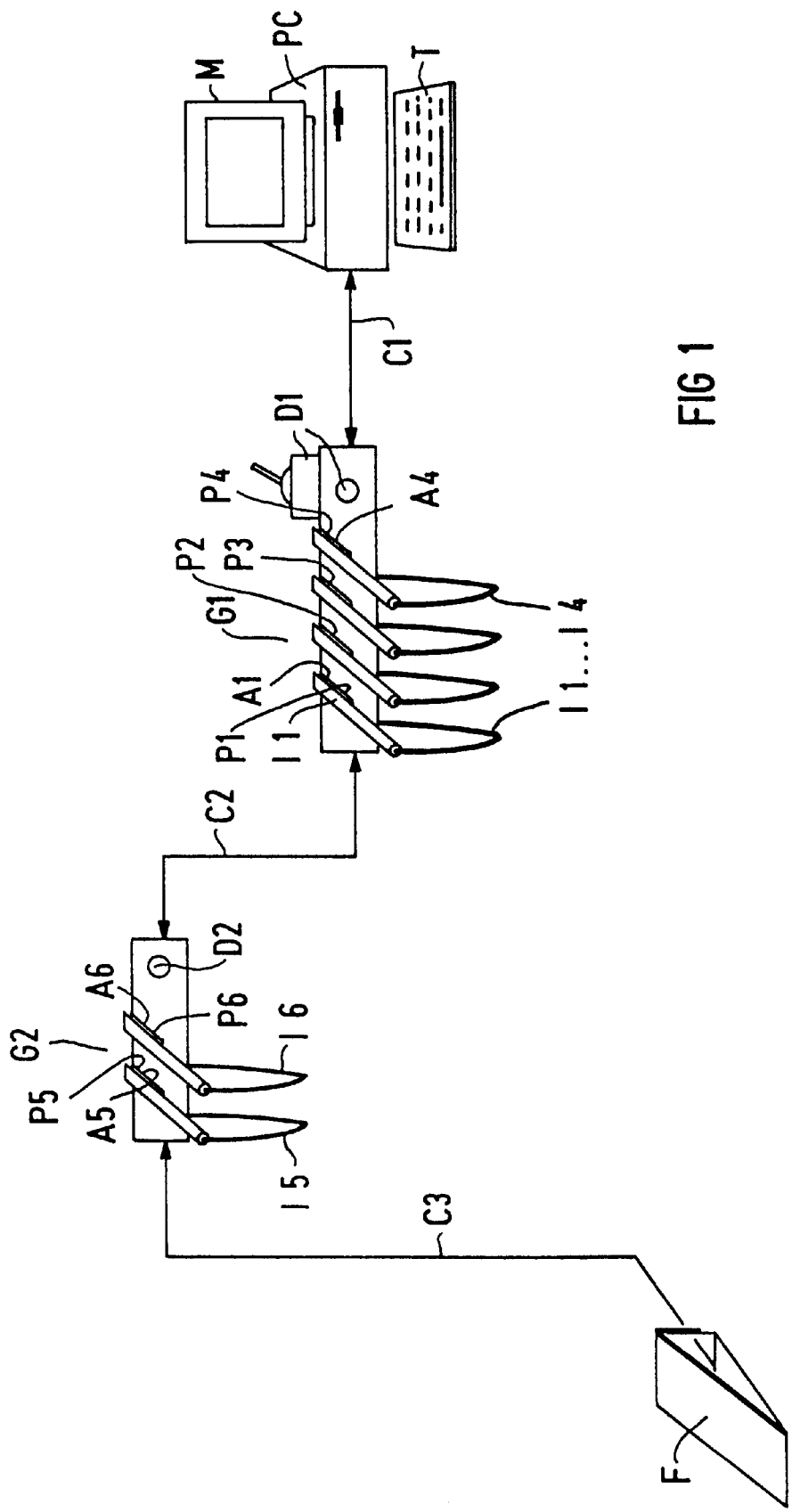
FIG. 1 is a schematic illustration of a dental apparatus of the present invention.

The principles of the present invention are particularly useful when incorporated in a dental apparatus schematically illustrated in FIG. 1. The dental apparatus has a first peripheral device G1 that contains a first group of four deposit devices or stations A1 through A4 for hose-bound or cable-bound hand-held instruments or dental handpieces 11 through 14, which are deposited therein. A second peripheral device G2 that contains a second group of two additional hand-held instruments 15 and 16 held in deposits A5 and A6 is provided. The instruments 11 through 14 can, for example, be standard drilling and grinding instruments suitable for tooth preparation, whereas the instruments 15 and 16 are hand-held instruments that can be image-acquiring instruments, for example hand-held instruments having an integrated video camera or x-ray camera.

The device G1 is connected by a cable C1 to the serial interface of a personal computer PC that has a keyboard T as well as a monitor M arranged in a known way. The device G1 contains an electronics module, to be set forth in greater detail later, which includes a logic circuit that is connected via a further or additional connecting cable C2 to the additional electronics module in the device G2. From the device G2, a third connecting cable C3, in turn, leads to a foot switch F.

All instruments 11 through 16 have sensors in the form of position indicators P1 through P6, which will acquire the removed or, respectively, deposited condition of each of the instruments. Such position indicators can be light barriers, as disclosed, for example, in U.S. Pat. No. 4,308,011, whose disclosure is incorporated herein by reference thereto. The position indicators forward an appropriate signal to the above-mentioned logic circuit that, in turn, forwards an information signal to the personal computer (PC) which then can potentially display the signal at the monitor M.

The foot switch F preferably comprises a plurality of switch positions that can be adjusted from a middle position in two opposite directions.

Figure 2:
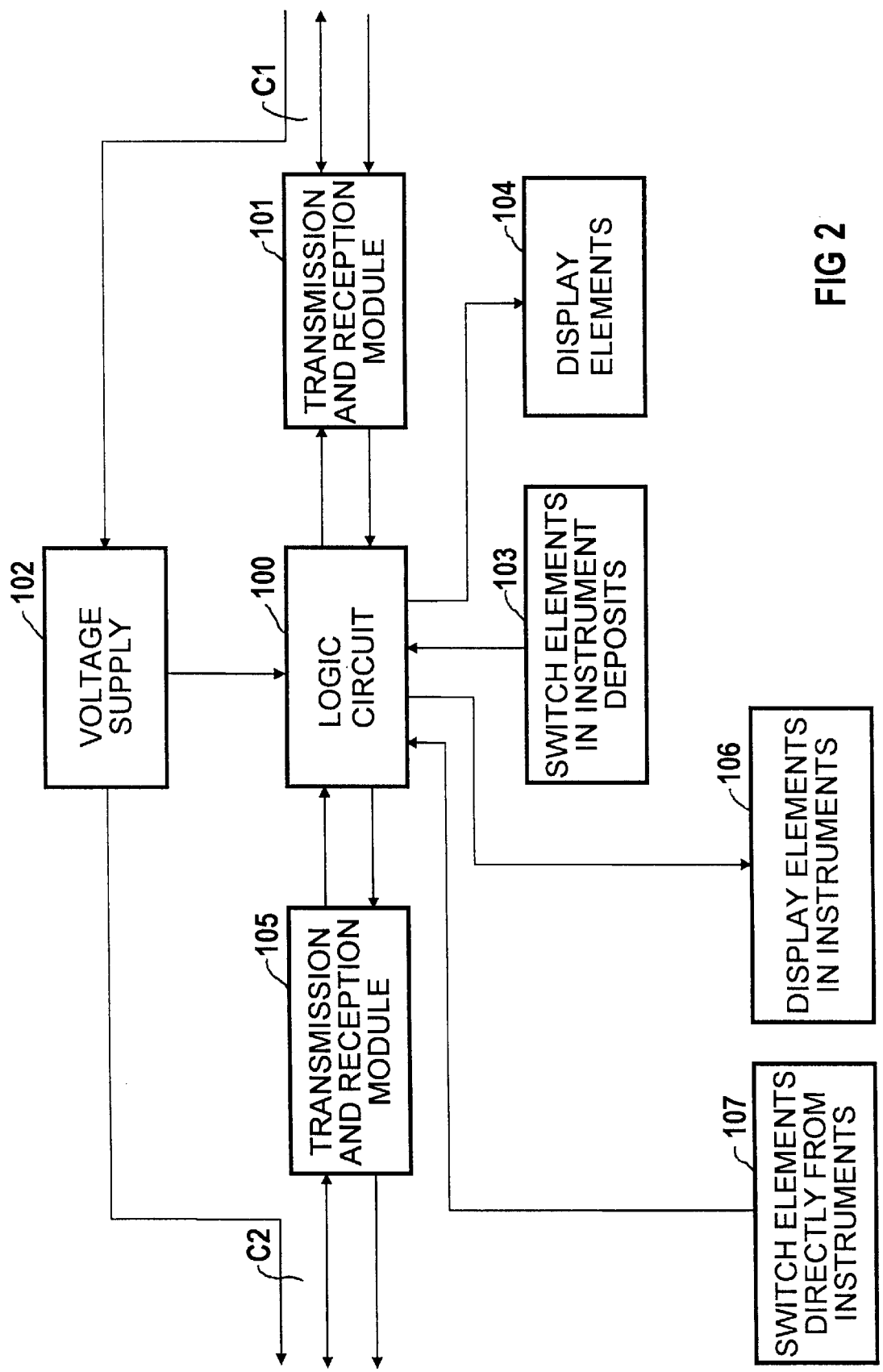
FIG. 2 is a block circuit diagram of the logic circuit.

The circuit-oriented structure of the PC-communicating instrument deposit shall be set forth with reference to the block circuit diagram in FIG. 2.

All incoming and outgoing logic statuses are switched via a logic circuit 100 (FIG. 2) that can preferably be a programmed IC. The logic circuit 100 is connected with a cable C1 to the standard interface of the personal computer PC of FIG. 1 through a transmission and reception module 101 (FIG. 2). A voltage supply 102 for the circuit preferably occurs via a serial interface proceeding from the personal computer PC, since this is standardly available. The logic circuit 100 receives signals from switch elements 103 that are located in the instrument deposits A1 through A6. In the present case, these are the position indicators P1 through P6 that report the deposited or, respectively, removed condition of the respective instrument. The signals are transmitted to the personal computer via the transmission and reception module 101. The logic circuit 100 forwards signals from the personal computer to display elements 104, which are referenced D1 and D2 in the devices G1 and G2 of FIG. 1.

When, as shown in the exemplary embodiment, a second peripheral device G2 is present, it is advantageous to connect the instrument deposits A5 and A6 to the interface of the personal computer cascaded in series. In the illustrated application, the device G2 also contains a corresponding second logic circuit (not shown in FIG. 2) and, as shown in FIG. 2, this second logic circuit is connected via a cable C2 to the logic circuit 100 in the device G1. Likewise, an additional transmission and reception module 105 is provided, and this exercises the same function as the module 101. Display elements 106 are likewise activated by the logic circuit that indicates operational readiness of the instruments, error messages or status functions such as speed. Switch elements 107 identify the instruments. These switch elements are arranged in the instruments themselves or in the supply hoses connected thereto. The signals proceeding from these switch elements are first forwarded to the logic circuit 100 and are then forwarded via the transmission module 101 to the personal computer PC. This arrangement has the advantage that only one serial interface at the personal computer need be occupied.

A few especially advantageous applications are set forth below.

Upon removal of an instrument 11 through 14 from its respective holder A1 through A4, the user program in the personal computer PC that is respectively allocated to the withdrawn instrument is activated by the logic circuit. When, for example, a drill instrument having an electric motor drive arranged in the instrument is removed from its deposit, then the control and/or monitoring program in the personal computer that is allocated to this instrument is activated. Upon deposit of the instrument, a neutral condition is set. When another instrument, for example having an integrated video camera, such as an instrument 15 or 16, is subsequently taken, then the logic circuit in the device G2 activates the respective program in the personal computer which is switched to the instrument program allocated for this instrument that has now been pulled.

With reference to the stored program, for example, a trigger switch present at the instrument or at the foot switch F can "freeze" a specific video frame if desired.

Individual instrument programs in the user program of the personal computer PC can, for example, be selected and activated with the foot switch F, which comprises a plurality of switch positions.

It is possible within the scope of the invention to expand the existing function of the trigger switch at the foot switch in that an additional significance is accorded to the temporal succession of triggering. For example, the function of the foot switch can be expanded by simple clicking, double clicking or holding the trigger switch. When the personal computer and the software monitoring the serial interface are not designed for differentiating between different switching events, the logic circuit in the personal computer will assume this task. Dependent on the switching sequence and switching duration, the logic circuit transmits a coded data word via the serial interface to the personal computer, which is informed of the switch action via a known code key. Such a data word is usually seven through eight bits long. This data word can be sent to the personal computer at every new action or use of an instrument.

Although various minor modifications may be suggested by those versed in the art, it should be understood that we wish to embody within the scope of the patent granted hereon all such modifications as reasonably and properly come within the scope of our contribution to the art.

We claim:

1. In a dental apparatus comprising a group of hand-held preparation instruments of different configurations being held in deposit devices, sensors being allocated to the deposit devices to acquire the configuration and deposit condition of the preparation instruments, instrument-related switch and display elements, and control means shared in common by the preparation instruments for displaying the instrument-related functions and for actuating these instruments with the assistance of a foot switch dependent on the removal and deposit of the instrument, the improvements comprising a second group of hand-held diagnostic instruments consisting of cameras for image acquiring, a personal computer with a keyboard and monitor being shared in common by the hand-held preparation instruments and the second group of hand-held diagnostic instruments, each of the instruments having data about instrument-related functions, a deposit having a sensor for each diagnostic instrument, a logic circuit, said preparation instruments and the diagnostic instruments being connected by the logic circuit to one interface of said personal computer, wherein the program installed in the personal computer for each instrument is activated by the logic circuit dependent on the removal of the instrument from the deposit.

2. In a dental apparatus according to claim 1, wherein said logic circuit is connected to switch and display elements so that bidirectional operating data that corresponds to the instruments and sensors allocated to the instruments are transmitted via the logic circuit and the interface to the personal computer.

3. In a dental apparatus according to claim 1, wherein means are present that indicate the operating condition of an instrument-related drive on the monitor.

4. In a dental apparatus according to claim 3, wherein deviations from the rated operating values of the drive are displayed on the monitor.

5. In a dental apparatus according to claim 1, wherein the foot switch is provided with a plurality of switch positions with which preferably instrument-related programs can be selected via the logic circuit.

6. In a dental apparatus according to claim 1, wherein said logic circuit is connected to a serial interface of the personal computer.

7. In a dental apparatus according to claim 1, wherein more than one instruments are connected to the interface of the personal computer cascaded in series.

8. In a dental apparatus according to claim 7, wherein a plurality of instruments are combined to form each group and a separate logic circuit is allocated to each group.

9. In a dental apparatus according to claim 1, wherein said logic circuit is constructed to recognize the type of temporal activation of the switch elements and converts this activation into a personal computer-recognizable code and transmits the code so that the information is bidirectionally transmitted in coded form.

10. In a dental apparatus according to claim 1, wherein the diagnostic instruments includes a video camera for intraoral observation.

11. In a dental apparatus according to claim 1, wherein the diagnostic instruments includes a video camera for extraoral observation.

12. In a dental apparatus according to claim 1, wherein the hand-held diagnostic instruments include an X-ray camera for receiving images and being receivable in one of the deposits.

13. In a dental apparatus according to claim 1, wherein the second group of hand-held diagnostic instruments has a separate logic circuit which is connected to the personal computer through the first-mentioned logic circuit.

\* \* \* \* \*